(12) United States Patent
Charles (10) Patent No.: US 12,274,642 B2
(45) Date of Patent: Apr. 15, 2025

(54) AIR TURBINE DRIVEN ROTARY VALVE FOR VITRECTOMY PROBE

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 416 days.

(21) Appl. No.: 17/813,402

(22) Filed: Jul. 19, 2022

(65) Prior Publication Data

US 2023/0058540 A1   Feb. 23, 2023

Related U.S. Application Data

(60) Provisional application No. 63/234,765, filed on Aug. 19, 2021.

(51) Int. Cl.
*A61F 9/007* (2006.01)
*F16K 11/074* (2006.01)
*F16K 31/42* (2006.01)

(52) U.S. Cl.
CPC ........ *A61F 9/00763* (2013.01); *F16K 11/074* (2013.01); *F16K 31/42* (2013.01)

(58) Field of Classification Search
CPC ................................. A61C 1/05; F01D 15/062
USPC .......................................................... 415/904
See application file for complete search history.

(56) References Cited

U.S. PATENT DOCUMENTS

| | | | |
|---|---|---|---|
| 4,117,597 A | 10/1978 | Trist et al. | |
| 4,318,695 A | 3/1982 | Lieb et al. | |
| 4,403,958 A * | 9/1983 | Lohn | A61C 1/05 433/126 |
| 4,530,356 A | 7/1985 | Helfgott et al. | |
| 4,642,051 A * | 2/1987 | Lohn | A61C 1/18 433/126 |
| 5,019,035 A | 5/1991 | Missirlian | |
| 5,176,628 A | 1/1993 | Charles et al. | |
| 7,677,890 B2 | 3/2010 | Turner | |
| 9,517,161 B2 | 12/2016 | Underwood | |
| 9,615,969 B2 | 4/2017 | Nissan | |
| 9,693,898 B2 | 7/2017 | Farley | |
| 10,383,766 B2 | 8/2019 | Farley | |

(Continued)

FOREIGN PATENT DOCUMENTS

DE   102017218491 A1   4/2019
FR   2679794 A1   2/1993

OTHER PUBLICATIONS

Charles, S., Fluidics and Cutter Dynamics, Physics matter in deciding on cut rates and duty cycles, Retinal Physician, Apr. 1, 2012, pp. 58-60, vol. 9.

(Continued)

*Primary Examiner* — Katherine M Shi
*Assistant Examiner* — Lindsey Bachman (57) ABSTRACT

Certain embodiments provide a vitrectomy probe including a housing, an actuator disposed inside the housing, a cutter coupled to the actuator and extending from the housing and an air turbine disposed inside the housing. The air turbine includes a rotor and a plurality of turbine blades coupled to the rotor. The vitrectomy probe includes a valve body interfacing with the rotor. During rotation of the air turbine, air is selectively routed to and from the actuator according to a rotational position of the rotor in relation to the valve body, thereby reciprocating the cutter.

15 Claims, 9 Drawing Sheets

(56) References Cited

U.S. PATENT DOCUMENTS

| | | | |
|---|---|---|---|
| 10,555,834 B2 | 2/2020 | Charles | |
| 10,729,582 B2 | 8/2020 | Biancalana | |
| 11,020,271 B2 | 6/2021 | Valencia | |
| 2008/0154292 A1 | 6/2008 | Huculak | |
| 2012/0221033 A1 | 8/2012 | Auld | |
| 2013/0158584 A1* | 6/2013 | Underwood | A61F 9/00763 606/171 |
| 2014/0171995 A1 | 6/2014 | Mcdonell | |
| 2014/0296900 A1 | 10/2014 | Barnes | |
| 2015/0327881 A1 | 11/2015 | Willhite | |
| 2016/0223090 A1 | 8/2016 | G. R. | |
| 2017/0071788 A1 | 3/2017 | Anderson | |
| 2017/0333252 A1 | 11/2017 | Biancalana | |
| 2018/0008463 A1 | 1/2018 | Charles | |
| 2018/0104101 A1 | 4/2018 | Lopez | |
| 2018/0369016 A1 | 12/2018 | Underwood | |
| 2019/0038460 A1 | 2/2019 | Peterson | |
| 2019/0314201 A1 | 10/2019 | Paydar | |

OTHER PUBLICATIONS

Dugel, P. U., MD. (Feb. 2009). Early Clincal Experience With the Constellation Vision System. Safety is always a top priority, but increased efficiency is a critical benefit for the ASC. Retinal Physician. Retrieved Mar. 1, 2018, from https://www.retinalphysician.com/supplements/2009/february-2009/special-edition/.

\* cited by examiner

AIR TURBINE DRIVEN ROTARY VALVE FOR VITRECTOMY PROBE

PRIORITY CLAIM

This application claims the benefit of priority of U.S. Provisional Patent Application Ser. No. 63/234,765 titled "AIR TURBINE DRIVEN ROTARY VALVE FOR VITRECTOMY PROBE," filed on Aug. 19, 2021, whose inventor is Steven T. Charles, which is hereby incorporated by reference in its entirety as though fully and completely set forth herein.

BACKGROUND

Certain ophthalmic surgical procedures require cutting and removing portions of the vitreous humor, a transparent gel-like material that fills the posterior segment of the eye. The vitreous humor, or vitreous, is composed of numerous microscopic fibrils that may attach to the retina. Therefore, cutting and removing the vitreous must be done with great care to avoid traction on the retina, the separation of the retina from the retinal pigment epithelium and choroid, a retinal tear, or, in the worst case, cutting and removal of the retina itself. In particular, delicate operations such as mobile tissue management (e.g., cutting and removal of vitreous near a detached portion of the retina or a retinal tear), vitreous base dissection, and cutting and removal of membranes are particularly difficult.

Conventional vitrectomy probes can be divided into two types: axial or "guillotine style" probes and rotational probes. An axial or guillotine style probe has an inner cutting member (also referred to as a "cutter") that reciprocates in a translational manner along its longitudinal axis. The inner cutting member is positioned within an outer cutting member that includes a port at its distal end. Vitreous and/or membranes are aspirated into the open port of the outer cutting member. The vitreous and/or membranes are sheared as the inner cutting member reciprocates. The cut tissue is then aspirated away from the eye. The inner cutting member may reciprocate at a rate between several tens to several hundred times per second.

A rotational or rotary probe has an inner cutting member that rotates at a high rate around its longitudinal axis. In general, rotational probes use either continuous or reciprocating rotation (e.g., using limited rotary action drive mechanisms that limit angular rotation) of the inner cutting member. Undesired winding and/or tearing (as opposed to cutting) of the fibrils may occur with the use of continuous rotation.

During axial or rotational reciprocation of the cutter as described above, an undesirable pumping action or pulse flow may be produced through the port in the distal end of the outer cutting member. The pulse flow pushes fluid out of the port as the inner cutting member moves towards the port and draws additional fluid into the port as the inner cutting member moves away from the port. In certain cases, the pulse flow can damage the retina, lens capsule or iris, especially when pulling on collagen fibrils attached to the peripheral retina.

In both types of vitrectomy probes, the cutter is powered by a pneumatic vitrectomy machine (also referred to as a "surgical console") including one or more high-speed pneumatic solenoid valves (also referred to as "drive valves"). The cutter may be powered by pressurized air that is alternately directed to two output ports of the surgical console through action of the solenoid valves. The air pressure pulses are carried from the output ports of the surgical console through multiple feet of elastomeric tubing before being applied to a corresponding chamber of the actuator for driving reciprocating motion of the cutter. Unfortunately, the solenoid valves increase the cost and noise of the surgical console, and vibration of the tubing produces additional noise and heat. In addition, by the time the air pressure pulses reach the actuator, substantial pulse broadening has occurred which further exacerbates the issues related to pulse flow within the eye as described above.

Therefore, there is a need for improved vitrectomy probes that address at least some of the disadvantages outlined above.

BRIEF SUMMARY

The present disclosure relates generally to a vitrectomy probe.

Certain embodiments described herein provide a vitrectomy probe including a housing, an actuator disposed inside the housing, a cutter coupled to the actuator and extending from the housing and an air turbine disposed inside the housing. The vitrectomy probe includes a valve body interfacing with the rotor. The air turbine includes a rotor and a plurality of turbine blades coupled to the rotor. During rotation of the air turbine, air is selectively routed to and from the actuator according to a rotational position of the rotor in relation to the valve body, thereby reciprocating the cutter.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

As described above, conventional vitrectomy probes rely on valving in the surgical console to alternately direct air pressure pulses through two corresponding lengths of tubing, which increases cost and noise of the surgical console, produces additional noise and heat within the tubing, and results in substantial air pressure pulse broadening which further exacerbates the issues related to pulse flow within the eye. Certain embodiments described in the present disclosure attempt to overcome these deficiencies by providing a vitrectomy probe with an air turbine driven rotary valve, thereby replacing the pneumatic valves in the surgical console. In certain embodiments, relocating the valving from the surgical console to the vitrectomy probe reduces or prevents broadening of the air pressure pulses that normally occurs in the elastomeric tubing. In addition, vibration of the elastomeric tubing due to the air pressure pulses is also reduced or prevented. In certain embodiments, higher cutting rates can mitigate pulse flow induced damage by reducing a distance over which the fibers are pulled prior to being sheared by the cutter.

Figure 1A:
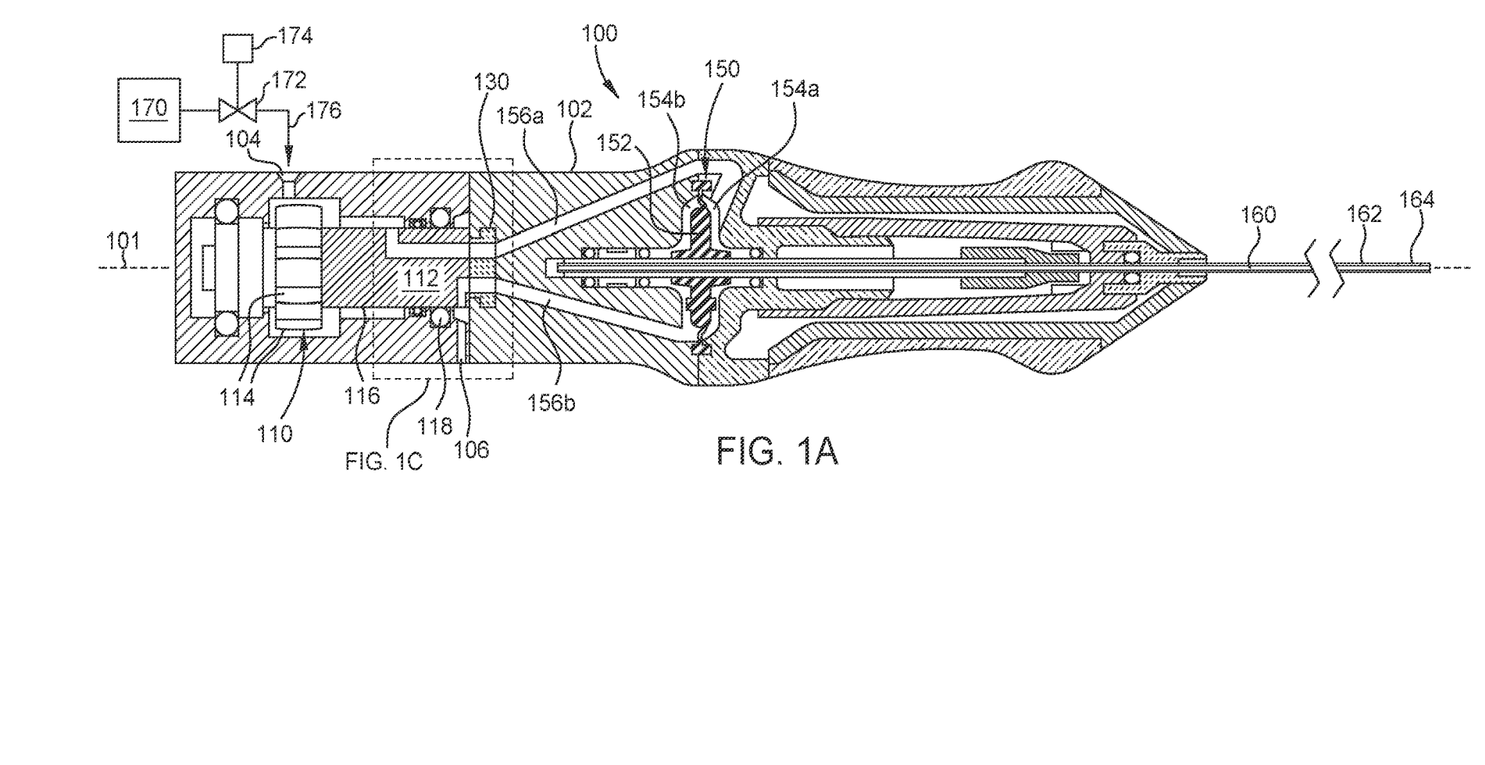
FIG. 1A illustrates a cross-sectional view of a vitrectomy probe, according to certain embodiments.
Figure 1B:
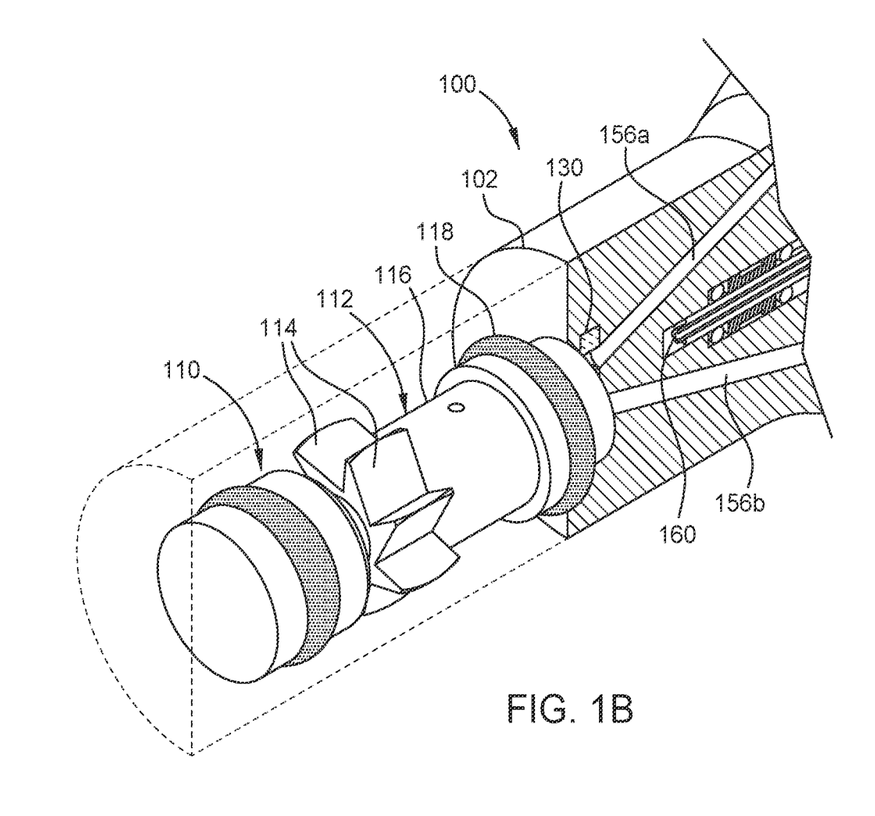
FIG. 1B illustrates a partial cut-away isometric view of the vitrectomy probe of FIG. 1A, according to certain embodiments.

FIG. 1A illustrates a cross-sectional view of a vitrectomy probe 100, according to certain embodiments. FIG. 1B illustrates a partial cut-away isometric view of vitrectomy probe 100 of FIG. 1A, according to certain embodiments. FIG. 1A and FIG. 1B are, therefore, described together herein for clarity.

Vitrectomy probe 100 generally includes a housing 102, an air turbine 110 disposed inside housing 102, a valve body 130 disposed inside housing 102, an actuator 150 disposed inside housing 102, and a cutter 160 coupled to actuator 150 and extending from housing 102. As shown in FIG. 1A, housing 102, air turbine 110, valve body 130, actuator 150 and cutter 160 are axially aligned parallel to center axis 101. Vitrectomy probe 100 is coupled to an air supply source 170 through a length of tubing 176, such as elastomeric tubing. The flow of air through tubing 176 is regulated by an air supply valve 172 that is actuated using a controller 174. In certain embodiments, air supply valve 172 is a pneumatic flow control valve for regulating output flow. In certain embodiments, air supply source 170, air supply valve 172, and controller 174 are disposed in or coupled to a surgical console.

As shown in FIG. 1A, housing 102 includes a single inlet 104 and a single outlet 106. Inlet 104 is in fluid communication with air turbine 110, valve body 130, and actuator 150. In general, rotation of air turbine 110 is driven by air flow from inlet 104 to actuator 150, as described in more detail below. In practice, an actuation rate of cutter 160 is adjusted based on air pressure applied to inlet 104. Outlet 106 is in fluid communication with actuator 150 for exhausting air from actuator 150.

Air turbine 110 generally includes a rotor 112 and a plurality of turbine blades 114 coupled to rotor 112. Rotor 112 and valve body 130 collectively form a valve mechanism (also referred to as a "rotary valve") having an interface that regulates air flow to actuator 150 for reciprocating cutter 160. The movable part of the valve mechanism is integral with rotor 112. Therefore, during rotation of air turbine 110, air is selectively routed to and from actuator 150 according to a rotational position of rotor 112 in relation to valve body 130. In other words, the rotational position of rotor 112 in relation to valve body 130 controls air flow through the interface of the valve mechanism. Operation of the valve mechanism is described in more detail below. An outer surface 116 of rotor 112 is sealed with housing 102 to prevent fluid communication between inlet 104 and outlet 106. In the illustrated embodiments, sealing is provided by O-ring seal 118. However, other sealing mechanisms are also contemplated.

Valve body 130 has multiple apertures that are configured to route air from a distal end of rotor 112 to a corresponding chamber of actuator 150. In the illustrated embodiments, valve body 130 is coupled to housing 102. Alternatively, valve body 130 may be integral with housing 102. Valve body 130 is described in more detail below with respect to FIG. 1C.

Actuator 150 generally includes a diaphragm 152 coupled to cutter 160, a first chamber 154a located on a first side of diaphragm 152, and a second chamber 154b located on a second opposite side of diaphragm 152. First chamber 154a is in fluid communication with a corresponding aperture of valve body 130 through a first flow line 156a. Likewise, second chamber 154b is in fluid communication with a corresponding aperture of valve body 130 through a second flow line 156b. Thus, by controlling the rotational position of rotor 112 in relation to valve body 130, air from inlet 104 is selectively fed to either first or second chamber 154a-b of actuator 150 while air within the opposite chamber is simultaneously exhausted to outlet 106, as described in more detail below.

A proximal end of cutter 160 is coupled to actuator 150. A distal end of cutter 160 extends from housing 102. The distal end of cutter 160 is disposed inside an outer cutting member 162, which extends from a distal end of housing 102. Cutter 160 reciprocates in a direction parallel to center axis 101 as differential air pressure is applied to first and second chambers 154a-b of actuator 150, as described in more detail below. A port 164 is disposed in a radial wall of outer cutting member 162. Vitreous and/or membranes are aspirated into port 164 during cutting. The vitreous and/or membranes are sheared as cutter 160 reciprocates inside outer cutting member 162. The cut tissue is then aspirated away from the eye. Vitrectomy probe 100 comprises an axial or "guillotine style" probe in which actuator 150 and cutter 160 reciprocate in a direction parallel to center axis 101. Embodiments of the present disclosure may also be used with a rotary probe having an actuator and cutter that reciprocate in a circumferential direction about center axis 101.

Figure 1C:
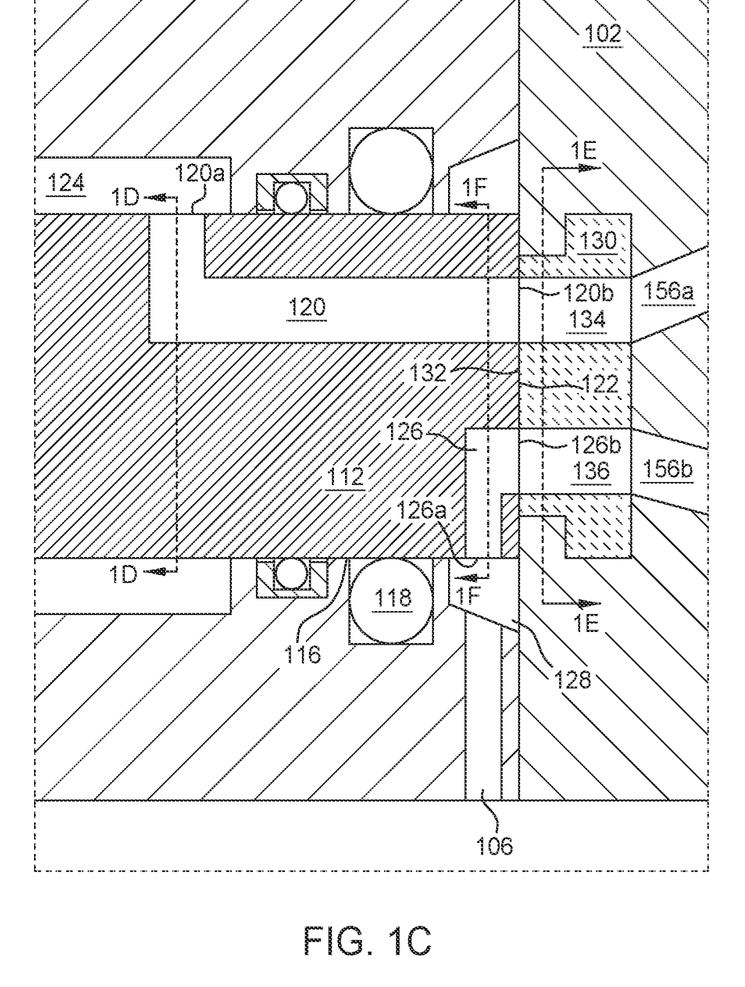
FIG. 1C illustrates an enlarged cross-sectional view of a portion of the vitrectomy probe of FIG. 1A, according to certain embodiments.
Figure 1D:
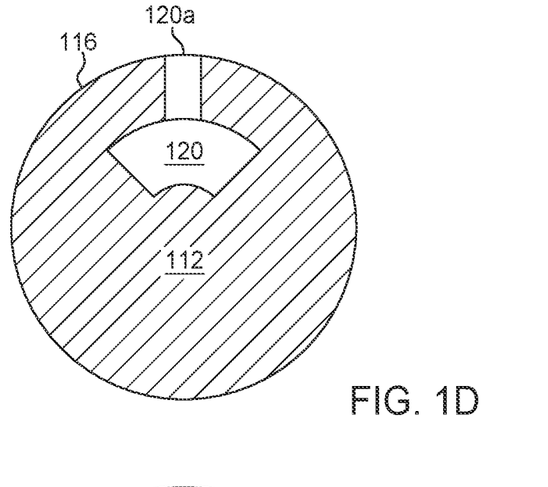
FIG. 1D illustrates a cross-sectional view taken along section line 1D-1D of FIG. 1C, according to certain embodiments.

FIG. 1C illustrates an enlarged cross-sectional view of a portion of vitrectomy probe 100 of FIG. 1A, according to certain embodiments. As shown in FIG. 1C, a first flow path 120 is disposed in rotor 112. First flow path 120 extends from a first radial opening 120a in outer surface 116 to a first distal opening 120b in a distal end 122 of rotor 112. First flow path 120 is further illustrated in FIG. 1D. First radial opening 120a is located in a proximal direction in relation to O-ring seal 118. Note that, as described herein, a proximal end or portion of the component refers to the end or the portion that is distanced further away from the patient's body during use thereof. On the other hand, a distal end or portion of a component refers to the end or the portion that is closer to a patient's body. First flow path 120 is in fluid communication with inlet 104 through a first annulus 124. First annulus 124 is disposed radially between outer surface 116 of rotor 112 and housing 102 to maintain continuous fluid coupling between inlet 104 and first flow path 120 at each possible rotational position of rotor 112.

A second flow path 126 is disposed in rotor 112. Like first flow path 120, second flow path 126 extends from a second radial opening 126a in outer surface 116 to a second distal opening 126b in distal end 122 of rotor 112. Second radial opening 126a is located in a distal direction in relation to O-ring seal 118. As shown in FIG. 1C, first radial opening 120a and second radial opening 126a are located 180° apart on rotor 112. In some other embodiments, the radial openings are aligned parallel to center axis 101 of rotor 112. Second flow path 126 is in fluid communication with outlet 106 through second annulus 128. Second flow path 126 is fluidly isolated from inlet 104. Like first annulus 124, second annulus 128 is disposed radially between outer surface 116 of rotor 112 and housing 102 to maintain continuous fluid coupling between second flow path 126 and outlet 106 at each possible rotational position of rotor 112.

A proximal end 132 of valve body 130 is in air-tight contact with distal end 122 of rotor 112. A first aperture 134 in proximal end 132 of valve body 130 is in fluid communication with first flow line 156a. A second aperture 136 in proximal end 132 of valve body 130 is in fluid communication with second flow line 156b.

Figure 1E:
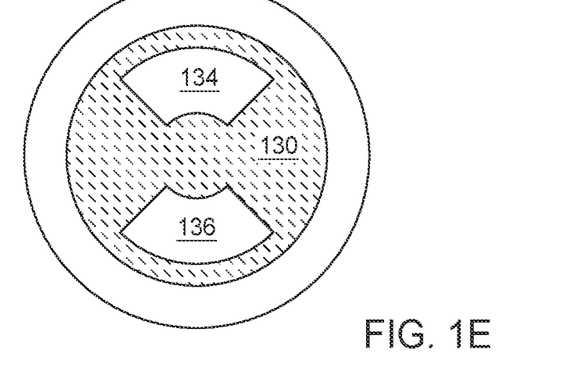
FIG. 1E illustrates a cross-sectional view taken along section line 1E-1E of FIG. 1C, according to certain embodiments.

FIG. 1E illustrates a cross-sectional view taken along section line 1E-1E of FIG. 1C, according to certain embodiments. As shown in FIG. 1E, first aperture 134 and second aperture 136 each comprise arc-shaped segments located on radially opposite sides of proximal end 132 of valve body 130. First aperture 134 and second aperture 136 each have an angle of about 60 degrees to about 120 degrees.

Figure 1F:
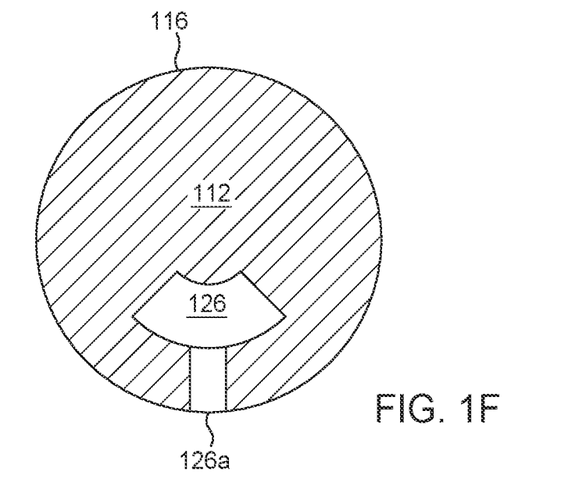
FIG. 1F illustrates a cross-sectional view taken along section line 1F-1F of FIG. 1C, according to certain embodiments.

FIG. 1F illustrates a cross-sectional view taken along section line 1F-1F of FIG. 1C, according to certain embodiments. As shown in FIG. 1F, first distal opening 120b and second distal opening 126b of rotor 112 each comprise arc-shaped segments having an angle of about 60 degrees to about 120 degrees. First distal opening 120b and second distal opening 126b are located on radially opposite sides, or 180° apart, on distal end 122.

Referring collectively to FIGS. 1A-1F, operation of vitrectomy probe 100 is described below. When rotor 112 is in the position illustrated, first flow path 120 of rotor 112 is in fluid communication with first aperture 134 of valve body 130, thereby supplying air to first chamber 154a of actuator 150 to move cutter 160 in a proximal direction in relation to housing 102. When rotor 112 is in the position illustrated, outlet 106 of housing 102 is in fluid communication with second chamber 154b of actuator 150. In this position, air within second chamber 154b is exhausted through second aperture 136 of valve body 130, through second flow path 126 of rotor 112, and subsequently through outlet 106 of housing 102.

When rotor 112 is rotated 180° from the position illustrated, first flow path 120 of rotor 112 is in fluid communication with second aperture 136 of valve body 130, thereby supplying air to second chamber 154b of actuator 150 to move cutter 160 in a distal direction in relation to housing 102. When rotor 112 is rotated 180° from the position illustrated, outlet 106 of housing 102 is in fluid communication with first chamber 154a of actuator 150. In this position, air within first chamber 154a is exhausted through first aperture 134 of valve body 130, through second flow path 126 of rotor 112, and subsequently through outlet 106 of housing 102.

Figure 2A:
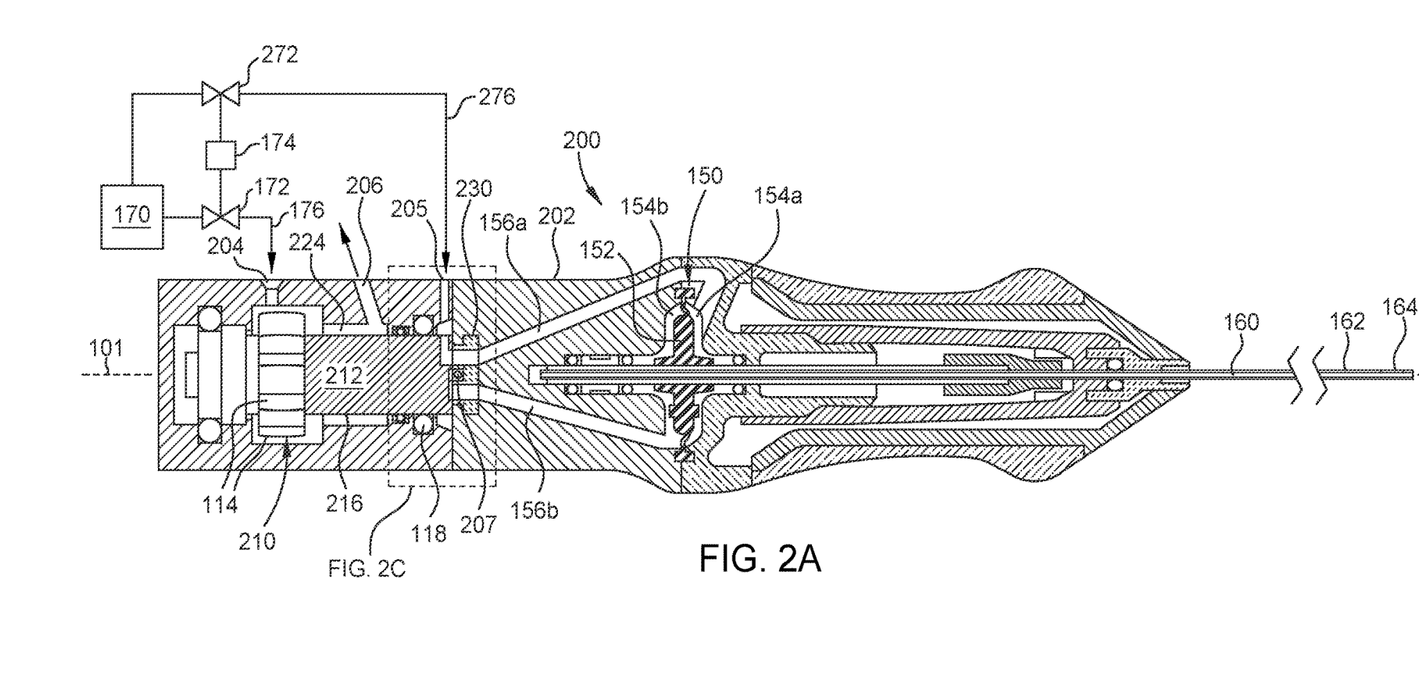
FIG. 2A illustrates a cross-sectional view of another vitrectomy probe, according to certain embodiments.
Figure 2B:
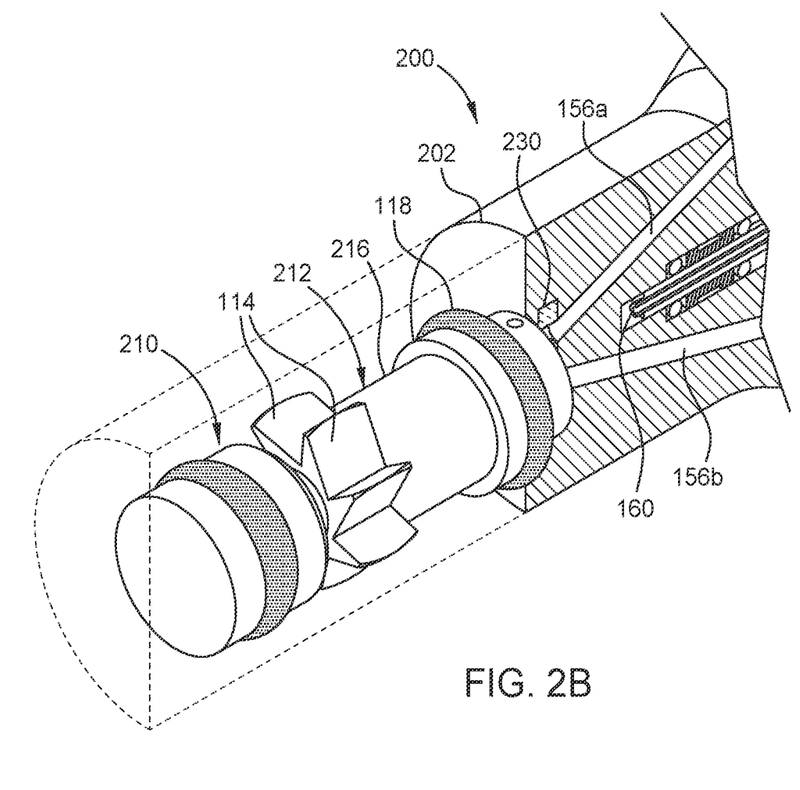
FIG. 2B illustrates a partial cut-away isometric view of the vitrectomy probe of FIG. 2A, according to certain embodiments.

FIG. 2A illustrates a cross-sectional view of another vitrectomy probe 200, according to certain embodiments. FIG. 2B illustrates a partial cut-away isometric view of vitrectomy probe 200 of FIG. 2A, according to certain embodiments. FIG. 2A and FIG. 2B are, therefore, described together herein for clarity.

Vitrectomy probe 200 has separate flow paths for independently driving air turbine 210 and actuator 250. This is in contrast to vitrectomy probe 100 described above, in which air turbine 110 and actuator 150 are both driven by the same air flow coming from inlet 104. As shown in FIG. 2A, vitrectomy probe 200 is coupled to air supply source 170 through a second length of tubing 276. The flow of air through tubing 276 is regulated by a second air supply valve 272 that is actuated using controller 174. In certain embodiments, second air supply valve 272 is a pneumatic flow control valve for regulating output flow similar to air supply valve 172. In certain embodiments, air supply valve 272 is disposed in or coupled to a surgical console. As shown in FIG. 2A, housing 202 includes a first inlet 204 and a first outlet 206 in fluid communication with first inlet 204. First inlet 204 and first outlet 206 are in fluid communication with blades 114 of air turbine 210. In general, rotation of air turbine 210 is driven by air flow from first inlet 204 to first outlet 206 through first annulus 224. First annulus 224 is disposed radially between outer surface 216 of rotor 212 and housing 202. In practice, an actuation rate of cutter 160 is adjusted based on air pressure applied to first inlet 204.

Housing 202 includes a second inlet 205 fluidly isolated from first inlet 204 and first outlet 206. Outer surface 216 of rotor 212 is sealed with housing 202 to prevent fluid communication between second inlet 205 and either of first inlet 204 or first outlet 206. Second inlet 205 is provided for supplying air to actuator 150. Housing 202 further includes a second outlet 207 for exhausting air from actuator 150. Note that, when viewing vitrectomy probe 200 as shown in FIG. 2A, second outlet 207 of housing 202 is oriented into the plane of the page as shown more clearly in FIG. 2E.

Figure 2C:
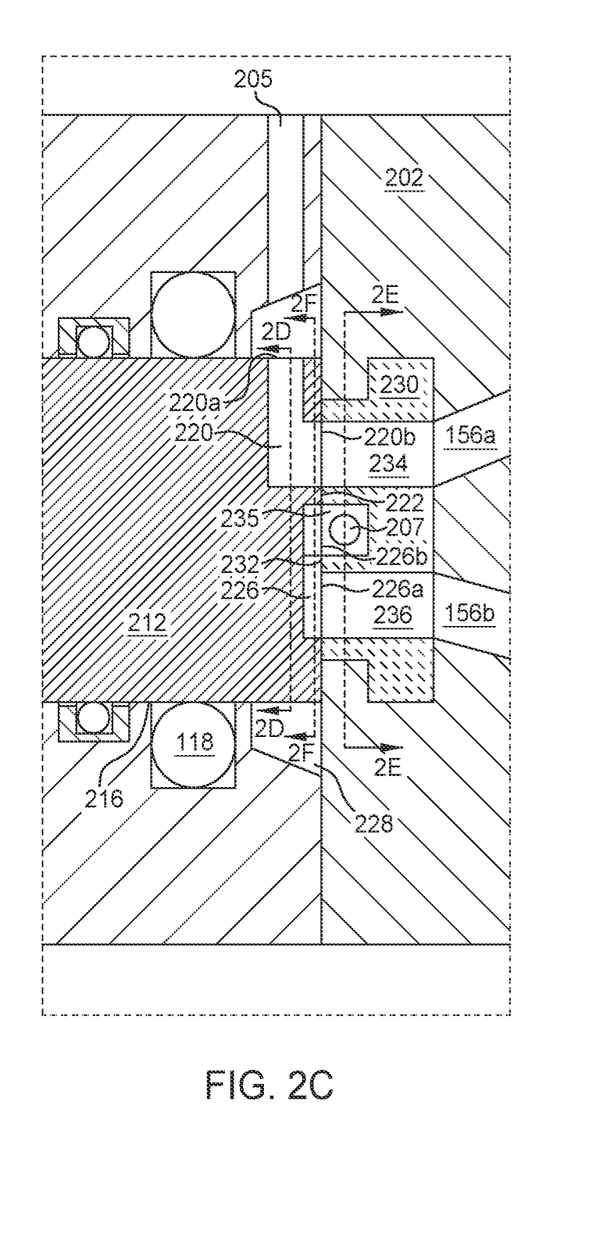
FIG. 2C illustrates an enlarged cross-sectional view of a portion of the vitrectomy probe of FIG. 2A, according to certain embodiments.
Figure 2D:
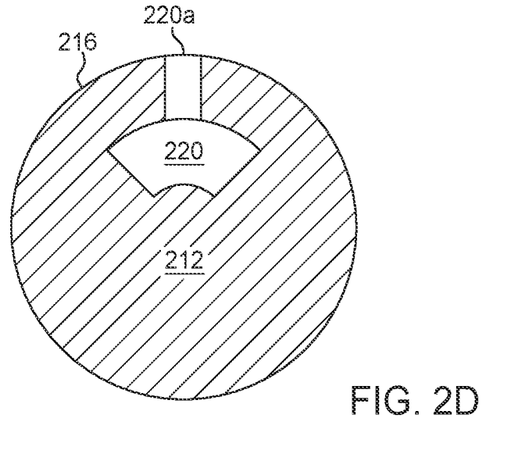
FIG. 2D illustrates a cross-sectional view taken along section line 2D-2D of FIG. 2C, according to certain embodiments.

FIG. 2C illustrates an enlarged cross-sectional view of a portion of vitrectomy probe 200 of FIG. 2A, according to certain embodiments. As shown in FIG. 2C, a first flow path 220 disposed in rotor 212 is in fluid communication with second inlet 205, which is in contrast to the design of vitrectomy probe 100 (shown in FIG. 1C). First flow path 220 extends from a first radial opening 220a in outer surface 216 to a first distal opening 220b in a distal end 222 of rotor 212. First flow path 220 is further illustrated in FIG. 2D. First radial opening 220a is located in a distal direction in relation to O-ring seal 118. First flow path 220 is in fluid communication with second inlet 205 through second annulus 228. Second annulus 228 is disposed radially between outer surface 216 of rotor 212 and housing 202 to maintain continuous fluid coupling between second inlet 205 and first flow path 220 at each possible rotational position of rotor 212.

A second flow path 226 is disposed in distal end 222 of rotor 212. Second flow path 226 is fluidly isolated from second inlet 205. In contrast to vitrectomy probe 100 (shown in FIG. 1C), second flow path 226 does not extend to outer surface 216. Instead, second flow path 226 consists of a single distal opening having a first portion 226a and a second portion 226b located radially inwardly of first portion 226a. Second portion 226b is located at a radial center of rotor 212. Valve body 230 has a third aperture 235 formed in proximal end 232, which is aligned axially with second portion 226b of second flow path 226. Third aperture 235 is in fluid communication with second outlet 207 of housing 202. Because second portion 226b and third aperture 235 are each located on center axis 101, fluid communication is maintained therebetween at each possible rotational position of rotor 212, thereby enabling air to be continuously exhausted through second outlet 207.

Figure 2E:
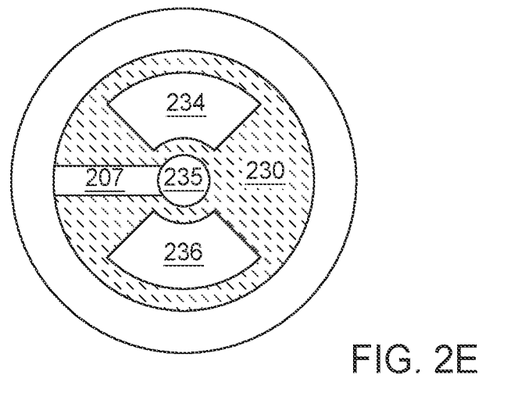
FIG. 2E illustrates a cross-sectional view taken along section line 2E-2E of FIG. 2C, according to certain embodiments.

FIG. 2E illustrates a cross-sectional view taken along section line 2E-2E of FIG. 2C, according to certain embodiments. As shown in FIG. 2E, first aperture 234 and second aperture 236 each comprise arc-shaped segments located on radially opposite sides of proximal end 232 of valve body 230. First aperture 234 and second aperture 236 each have an angle of about 60 degrees to about 120 degrees. In the illustrated embodiments, third aperture 235 is round.

Figure 2F:
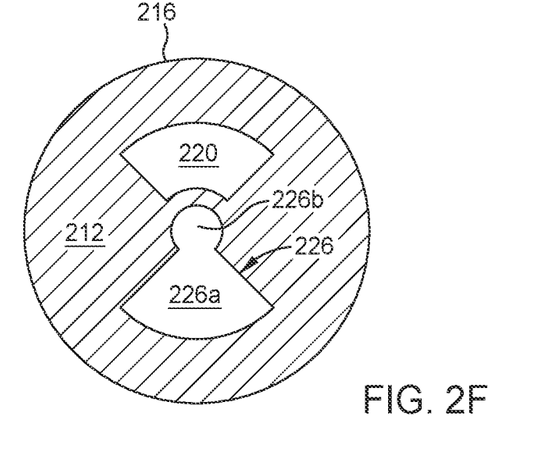
FIG. 2F illustrates a cross-sectional view taken along section line 2F-2F of FIG. 2C, according to certain embodiments.

FIG. 2F illustrates a cross-sectional view taken along section line 2F-2F of FIG. 2C, according to certain embodiments. As shown in FIG. 2F, first distal opening 220b and first portion 226a of second flow path 226 each comprise arc-shaped segments having an angle of about 60 degrees to about 120 degrees. First distal opening 220b and first portion 226a are located on radially opposite sides, or 180° apart, on distal end 222. In the illustrated embodiments, second portion 226b of second flow path 226 has a round shape corresponding to that of third aperture 235 of valve body 230.

Referring collectively to FIGS. 2A-2F, operation of vitrectomy probe 200 is described below. When rotor 212 is in the position illustrated, first flow path 220 of rotor 212 is in fluid communication with first aperture 234 of valve body 230, thereby supplying air to first chamber 154a of actuator 150 to move cutter 160 in a proximal direction in relation to housing 202. When rotor 212 is in the position illustrated, second outlet 207 of housing 202 is in fluid communication with second chamber 154b of actuator 150. In this position, air within second chamber 154b is exhausted through second aperture 236 of valve body 230, through second flow path 226 of rotor 212, and subsequently through third aperture 235 of valve body 230.

When rotor 212 is rotated 180° from the position illustrated, first flow path 220 of rotor 212 is in fluid communication with second aperture 236 of valve body 230, thereby supplying air to second chamber 154b of actuator 150 to move cutter 160 in a distal direction in relation to housing 202. When rotor 212 is rotated 180° from the position illustrated, second outlet 207 of housing 202 is in fluid communication with first chamber 154a of actuator 150. In this position, air within first chamber 154a is exhausted through first aperture 234 of valve body 230, through second flow path 226 of rotor 212, and subsequently through third aperture 235 of valve body 230.

Figure 3:
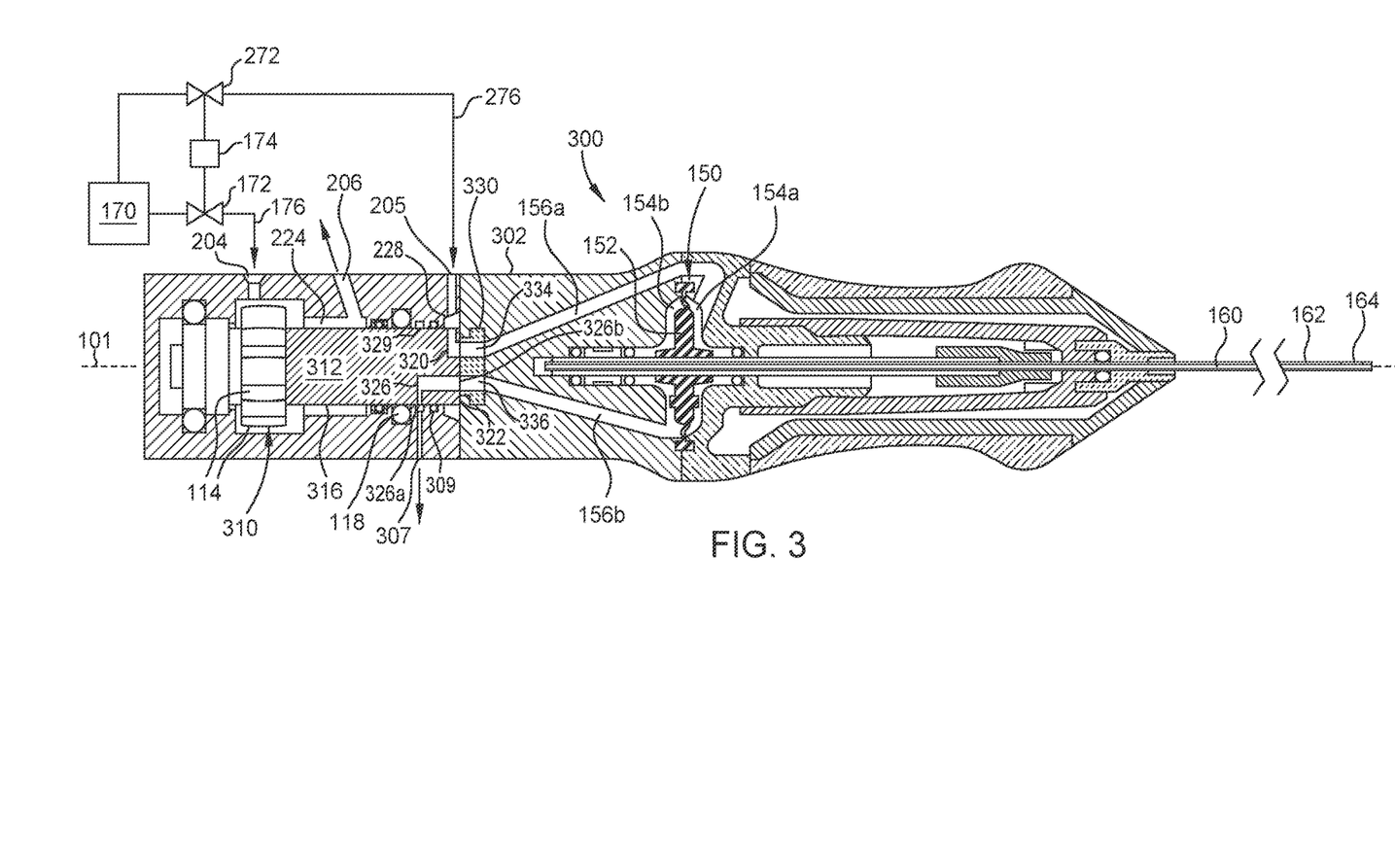
FIG. 3 illustrates a cross-sectional view of yet another vitrectomy probe, according to certain embodiments.

FIG. 3 illustrates a cross-sectional view of yet another vitrectomy probe 300, according to certain embodiments. Vitrectomy probe 300 combines elements of certain embodiments described above. In particular, vitrectomy probe 300 has separate flow paths for independently driving air turbine 310 and actuator 150 like vitrectomy probe 200. However, instead of exhausting air from actuator 150 into rotor 312 and back through valve body 330, air is exhausted through outer surface 316 of rotor 312 similar to vitrectomy probe 100. More particularly, vitrectomy probe 300 differs from vitrectomy probe 200 in that second flow path 326 extends from a second radial opening 326a in outer surface 316 to a second distal opening 326b in distal end 322 of rotor 312. Second flow path 326 is in fluid communication with second outlet 307 through a third annulus 329. Second flow path 326 is fluidly isolated from second inlet 205 by O-ring seal 309. Like second annulus 228, third annulus 329 is disposed radially between outer surface 316 of rotor 312 and housing 302 to maintain continuous fluid coupling between second flow path 326 and second outlet 307 at each possible rotational position of rotor 312.

Operation of vitrectomy probe 300 is described below. When rotor 312 is in the position illustrated, first flow path 320 of rotor 312 is in fluid communication with first aperture 334 of valve body 330, thereby supplying air to first chamber 154a of actuator 150 to move cutter 160 in a proximal direction in relation to housing 302. When rotor 312 is in the position illustrated, second outlet 307 of housing 302 is in fluid communication with second chamber 154b of actuator 150. In this position, air within second chamber 154b is exhausted through second aperture 336 of valve body 330, through second flow path 326 of rotor 312, and subsequently through second outlet 307 of housing 302.

When rotor 312 is rotated 180° from the position illustrated, first flow path 320 of rotor 312 is in fluid communication with second aperture 336 of valve body 330, thereby supplying air to second chamber 154b of actuator 150 to move cutter 160 in a distal direction in relation to housing 202. When rotor 312 is rotated 180° from the position illustrated, second outlet 307 of housing 302 is in fluid communication with first chamber 154a of actuator 150. In this position, air within first chamber 154a is exhausted through first aperture 334 of valve body 330, through second flow path 326 of rotor 312, and subsequently through second outlet 307 of housing 302.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A vitrectomy probe, comprising:
    a housing;
    an actuator disposed inside the housing;
    a cutter coupled to the actuator and extending from the housing;
    an air turbine disposed inside the housing, the air turbine comprising:
        a rotor; and
        a plurality of turbine blades coupled to the rotor; and
    a valve body interfacing with the rotor, wherein during rotation of the air turbine, air is selectively routed to and from the actuator according to a rotational position of the rotor in relation to the valve body, thereby reciprocating the cutter.

2. The vitrectomy probe of claim 1, wherein an actuation rate of the cutter is adjusted based on air pressure applied to an inlet of the air turbine.

3. The vitrectomy probe of claim 1, wherein the rotor comprises:
    an outer surface sealed with the housing; and
    a first flow path in the rotor from the outer surface to a distal end of the rotor, the first flow path configured to supply air to the actuator.

4. The vitrectomy probe of claim 3, wherein an opening of the first flow path in the distal end of the rotor comprises an arc-shaped segment having an angle of about 60 degrees to about 120 degrees.

5. The vitrectomy probe of claim 3, wherein the valve body is coupled to or integral with the housing and configured to supply air from the first flow path of the rotor to a corresponding chamber of the actuator.

6. The vitrectomy probe of claim 5, wherein the valve body comprises:
a proximal end in air-tight contact with the distal end of the rotor;
a first aperture in the proximal end of the valve body in fluid communication with a first chamber of the actuator; and
a second aperture in the proximal end of the valve body in fluid communication with a second chamber of the actuator.

7. The vitrectomy probe of claim 6, wherein the first aperture and second aperture of the valve body comprise arc-shaped segments located on radially opposite sides of the proximal end of the valve body.

8. The vitrectomy probe of claim 7, wherein the arc-shaped segments of the first aperture and second aperture of the valve body each have an angle of about 60 degrees to about 120 degrees.

9. The vitrectomy probe of claim 6, wherein:
when the rotor is in a first rotational position, the first flow path of the rotor is in fluid communication with the first aperture of the valve body, thereby supplying air to the first chamber of the actuator to move the cutter in a first direction, and
when the rotor is in a second rotational position, the first flow path of the rotor is in fluid communication with the second aperture of the valve body, thereby supplying air to the second chamber of the actuator to move the cutter in a second direction opposite the first direction.

10. The vitrectomy probe of claim 9, wherein:
when the rotor is in the first rotational position, a second flow path in the rotor is in fluid communication with the second aperture of the valve body, thereby exhausting air from the second chamber of the actuator, and
when the rotor is in the second rotational position, the second flow path in the rotor is in fluid communication with the first aperture of the valve body, thereby exhausting air from the first chamber of the actuator.

11. The vitrectomy probe of claim 6, wherein the rotor further comprises a second flow path therein, the second flow path extending from the distal end to the outer surface, the second flow path in fluid communication with an outlet of the housing.

12. The vitrectomy probe of claim 6, wherein:
the rotor further comprises a second flow path in the distal end of the rotor,
the valve body further comprises a third aperture in the proximal end of the valve body,
the third aperture is aligned axially with a portion of the second flow path located at a radial center of rotor, and
the third aperture is in fluid communication with an outlet of the housing.

13. The vitrectomy probe of claim 1, wherein the housing comprises:
an inlet in fluid communication with the air turbine and the actuator, wherein rotation of the air turbine is driven by air flow from the inlet to the actuator; and
an outlet for exhausting air from the actuator.

14. The vitrectomy probe of claim 1, wherein the housing comprises:
a first inlet;
a first outlet in fluid communication with the first inlet, wherein rotation of the air turbine is driven by air flow from the first inlet to the first outlet;
a second inlet fluidly isolated from the first inlet and the first outlet for supplying air to the actuator; and
a second outlet for exhausting air from the actuator.

15. The vitrectomy probe of claim 14, wherein an outer surface of the rotor is sealed with the housing to isolate the second inlet from the first inlet and the first outlet.

\* \* \* \* \*